United States Patent
Ota

(10) Patent No.: US 6,753,542 B2
(45) Date of Patent: Jun. 22, 2004

(54) DEFECT DETECTION APPARATUS AND STORAGE MEDIUM READABLE BY COMPUTER

(75) Inventor: Yoshinari Ota, Kamiina-gun (JP)

(73) Assignee: Olympus Optical Co., Ltd., Tokyo (JP)

( * ) Notice: Subject to any disclaimer, the term of this patent is extended or adjusted under 35 U.S.C. 154(b) by 53 days.

(21) Appl. No.: 10/394,379

(22) Filed: Mar. 21, 2003

(65) Prior Publication Data

US 2003/0178588 A1 Sep. 25, 2003

Related U.S. Application Data

(63) Continuation of application No. PCT/JP01/08295, filed on Sep. 25, 2001.

(30) Foreign Application Priority Data

Sep. 26, 2000 (JP) ........................................ 2000-292938

(51) Int. Cl.[7] .......................... G01N 21/88; G01N 21/00
(52) U.S. Cl. ............................... 250/559.45; 250/559.4; 250/559.41; 250/559.42; 250/559.44; 250/559.39; 250/559.46; 356/237.4; 356/237.5
(58) Field of Search ........................ 250/559.42, 559.07, 250/559.39, 559.41, 559.4, 559.44, 559.45, 559.46, 548; 356/237.2, 237.3, 237.4, 237.5, 394

(56) References Cited

U.S. PATENT DOCUMENTS

| | | | | |
|---|---|---|---|---|
| 5,252,836 A | * | 10/1993 | Matthews et al. | 250/559.18 |
| 5,363,187 A | * | 11/1994 | Hagiwara et al. | 356/237.3 |
| 5,936,254 A | * | 8/1999 | Aiyer et al. | 250/559.4 |
| 6,501,545 B2 | * | 12/2002 | Komuro et al. | 356/237.2 |
| 2002/0017620 A1 | * | 2/2002 | Oomori et al. | 250/559.4 |
| 2003/0057384 A1 | * | 3/2003 | Fukazawa | 250/559.45 |

FOREIGN PATENT DOCUMENTS

| | | |
|---|---|---|
| JP | 10-339701 A | 12/1998 |
| JP | 11-281585 A | 10/1999 |

OTHER PUBLICATIONS

English language translation of International Preliminary Examination Report issued in International Application No. PCT/JP01/08295, filed Sep. 25, 2001; Applicant: Olympus Optical Co., Ltd.

\* cited by examiner

Primary Examiner—David Porta
Assistant Examiner—David C. Meyer
(74) Attorney, Agent, or Firm—Frishauf, Holtz, Goodman & Chick, P.C.

(57) ABSTRACT

According to the present invention, there is disclosed a defect detection apparatus comprising an illuminating unit which irradiates an inspection object with illuminating light, and an image pickup unit which picks up an image of diffracted light from the inspection object to perform defect inspection of the inspection object from image data picked up by the image pickup unit, the apparatus further comprising a diffraction angle calculation unit to obtain the diffraction angle of the illuminating light with respect to the inspection object, which is optimum for picking up the image of the diffracted light, based on design information of the inspection object, and an illuminating setting unit which sets the angle of incidence of the illuminating unit to the diffraction angle calculated by the diffraction angle calculation unit.

11 Claims, 2 Drawing Sheets

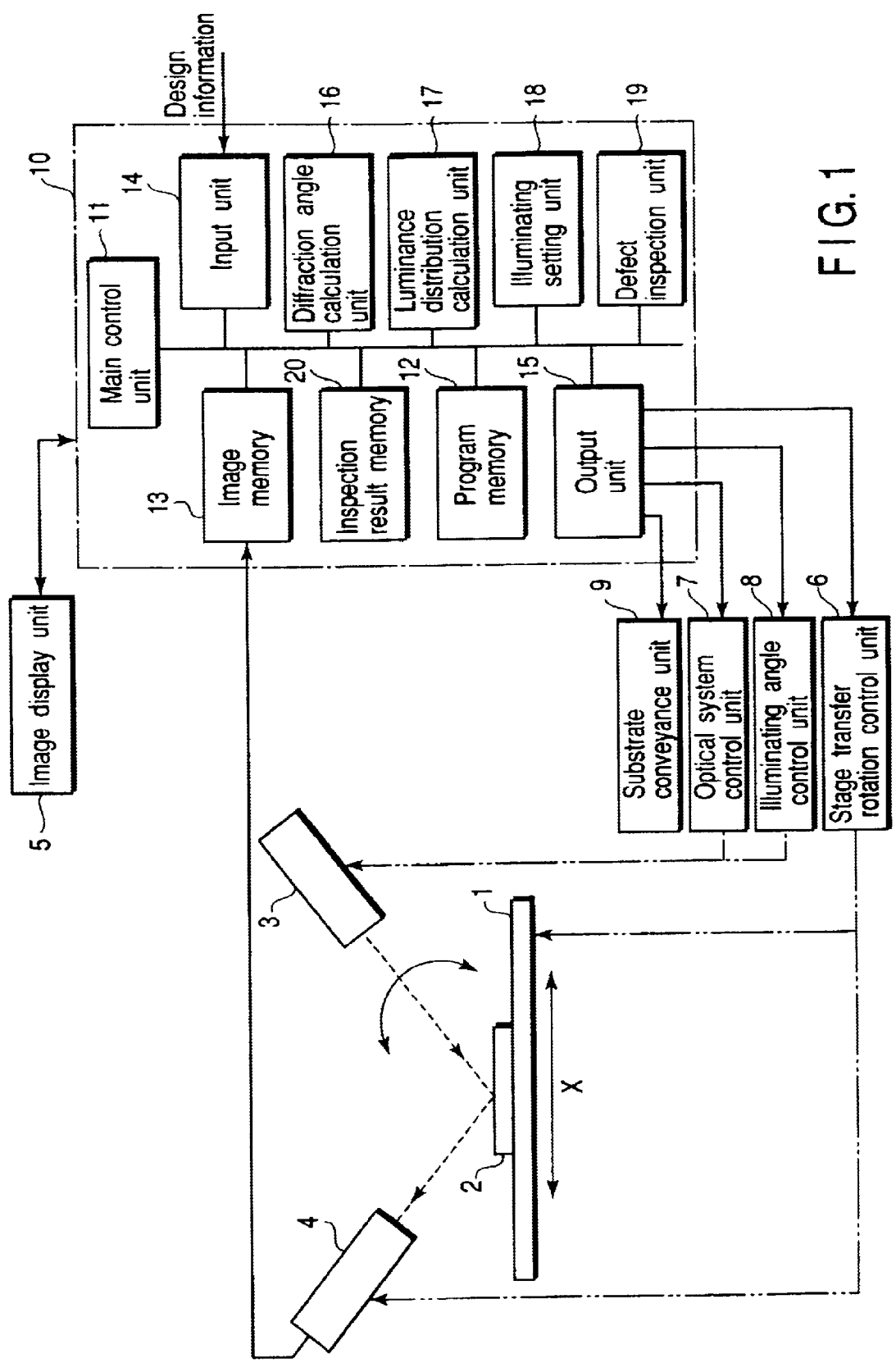
F I G. 1

DEFECT DETECTION APPARATUS AND STORAGE MEDIUM READABLE BY COMPUTER

CROSS-REFERENCE TO RELATED APPLICATIONS

This is a Continuation Application of PCT Application No. PCT/JP01/08295, filed Sep. 25, 2001, which was not published under PCT Article 21(2) in English.

This application is based upon and claims the benefit of priority from the prior Japanese Patent Application No. 2000-292938, filed Sep. 26, 2000, the entire contents of which are incorporated herein by reference.

BACKGROUND OF THE INVENTION

1. Field of the Invention

The present invention relates to a defect detection apparatus which irradiates inspection objects such as a semiconductor wafer with an illuminating light and performs defect inspection based on an image of the light from the inspection object, and a storage medium readable by a computer, in which a program is stored.

2. Description of the Related Art

For example, in a semiconductor manufacturing process, macro inspection of damage, dust, surface irregularity, dirt, and the like in a semiconductor wafer surface is performed. This macro inspection comprises: irradiating the semiconductor wafer surface with an illuminating light; picking up images of regular reflected light, diffracted light, and scattered light by an image pickup apparatus; and image-processing the image data to detect defects such as damage, dust, surface irregularity, and dirt in the semiconductor wafer surface.

FIG. 3 is a schematic diagram of a macro inspection apparatus according to related art. A semiconductor wafer 2 is laid on a stage 1, an illuminating unit 3 is disposed obliquely above the wafer, and an image pickup unit 4 is disposed in an opposite position with respect to the illuminating unit 3 with respect to the semiconductor wafer 2. In the macro inspection apparatus, when the semiconductor wafer 2 is irradiated with the illuminating light from the illuminating unit 3, and the image of a diffracted light from the semiconductor wafer 2 is picked up by the image pickup unit 4, an illuminating angle is variably set with respect to the semiconductor wafer 2 in order to detect the diffracted light.

In the setting method of the illuminating angle, while the semiconductor wafer 2 is irradiated with the illuminating light from the illuminating unit 3, the illuminating angle, that is, the inclination angle of the illuminating unit 3 with respect to the semiconductor wafer 2 is varied, for example, in a range of +20° to −20°. Subsequently, the image of the diffracted light from the semiconductor wafer 2 is picked up by the image pickup unit 4, the angle at which primary diffracted light can be taken in is obtained from the image data, and the illuminating unit 3 is set to the angle.

However, the semiconductor wafers 2 to be inspected include a wafer in which the shape and direction of the pattern of a formed chip differ with each type of wafer, and a wafer in which the pitch of the pattern differs. It is assumed that these semiconductor wafers 2 are inspected. Then, every time the type of the semiconductor wafer 2 changes, the illuminating angle is varied, for example, in a range of +20° to −20°. While the picked-up image data is referred to, the angle of incidence for satisfactorily taking in the primary diffracted light has to be obtained to set the inclination angle of the illuminating unit 3, and much time is required for the inspection.

Moreover, because of a difference of the shape, direction, or pitch of the pattern of the chip formed in the semiconductor wafer 2, the angle of incidence and the direction for the image pickup unit to satisfactorily take in the diffracted light from the pattern on the semiconductor wafer 2 differ. Therefore, the illuminating unit 3 cannot necessarily be set to an angle and direction optimum for taking in the diffracted light.

An object of the present invention is to provide a defect detection apparatus in which illuminating light can be set to an optimum angle to take in diffracted light necessary for performing an inspection.

Another object of the present invention is to provide a storage medium readable by a computer, in which a program for setting the illuminating light to the optimum angle to take in the diffracted light necessary for performing the inspection is stored.

BRIEF SUMMARY OF THE INVENTION

According to the present invention, there is provided a defect detection apparatus comprising: an illuminating unit which irradiates an inspection object with an illuminating light; and an image pickup unit which picks up an image of a diffracted light from the inspection object to perform defect inspection of the inspection object from image data picked up by the image pickup unit, the apparatus further comprising: a diffraction angle calculation unit to obtain the diffraction angle of the illuminating light with respect to the inspection object, which is optimum for picking up the image of the diffracted light, based on design information of the inspection object; and an illuminating setting unit which sets the angle of incidence of the illuminating unit to the diffraction angle calculated by the diffraction angle calculation unit.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a diagram showing a configuration of a defect detection apparatus according to an embodiment of the present invention;

DETAILED DESCRIPTION OF THE INVENTION

An embodiment of the present invention will be described hereinafter with reference to the drawings.

Figure 3:
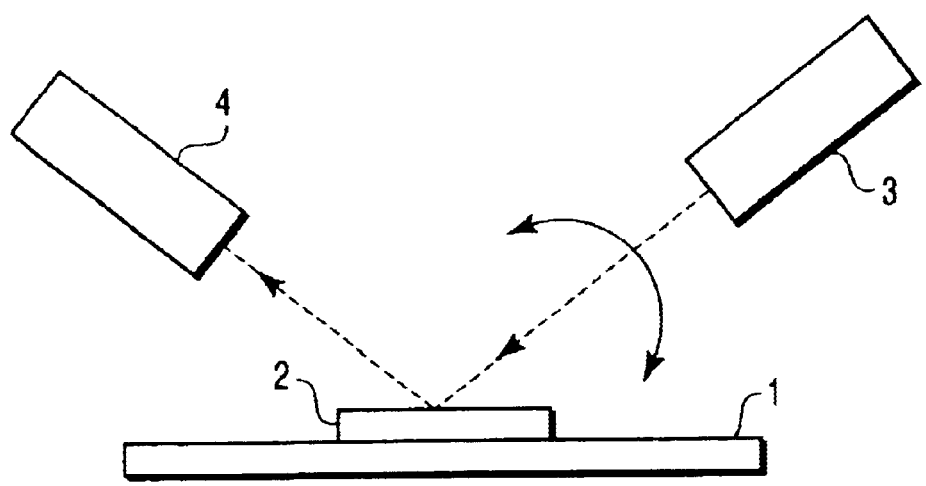
FIG. 3 is a schematic diagram of a macro inspection apparatus according to a related-art example.

FIG. 1 is a diagram showing a configuration of a defect detection apparatus according to the embodiment of the present invention. In FIG. 1, the same components as those of FIG. 3 are denoted with the same reference numerals. The defect detection apparatus shown in FIG. 1 detects defects with respect to inspection objects in which a regular pattern is formed in a substrate surface, such as a semiconductor wafer, and a glass substrate of a flat panel display such as a liquid crystal.

A semiconductor wafer 2 which is an inspection object is laid on a stage 1. Above the stage 1, a linear illuminating unit 3 and an image pickup unit 4 including a line sensor camera are disposed. The illuminating unit 3 is disposed so that an optical axis is inclined at a predetermined angle with respect to the surface of the semiconductor wafer 2, and irradiates the semiconductor wafer 2 surface with a linear illuminating light. The image pickup unit 4 is disposed so that the optical axis is inclined at the predetermined angle with respect to the surface of the semiconductor wafer 2, and picks up an image of diffracted light from the semiconductor wafer 2 surface generated by the illuminating from the illuminating unit 3 for each line. It is to be noted that the image pickup unit 4 is fixed in an inclined state of the optical axis at the predetermined angle. Moreover, the illuminating unit 3 is rotatably disposed so that an inclination angle with respect to the semiconductor wafer 2 surface can be adjusted in a predetermined range, and can be fixed in a desired position by an electric or mechanical stopper.

A detection apparatus main body 10 is connected to an image pickup unit 4, image display unit 5, stage transfer rotation control unit 6, optical system control unit 7, illuminating angle control unit 8, and substrate conveyance unit 9. The optical system control unit 7 and illuminating angle control unit 8 are connected to the illuminating unit 3. The stage transfer rotation control unit 6 is connected to the stage 1.

The detection apparatus main body 10 has a function of executing various types of control necessary for automatically setting an angle of incidence (inclination angle) and illuminating direction with respect to the semiconductor wafer 2 surface of the illuminating unit 3. The detection apparatus main body 10 sets an angle of incidence and illuminating direction of the illuminating unit 3, which are optimum for picking up an image of ±n-dimensional (natural number, n=1, 2, . . . ) diffracted light necessary for performing the defect inspection of the semiconductor wafer 2. In the detection apparatus main body 10, a main control unit 11 including a computer (CPU) is connected to a program memory 12, image memory 13, input unit 14, output unit 15, and inspection result memory 20. Furthermore, when the program stored in the program memory 12 is executed, functions of a diffraction angle calculation unit 16, luminance distribution calculation unit 17, illuminating setting unit 18, and defect inspection unit 19 work.

The program memory 12 can be read by the main control unit 11. In the program memory 12, a control program relating to the defect detection is stored comprising: obtaining the angle of incidence of the illuminating light with respect to the semiconductor wafer 2 by the fixed image pickup unit 4, which is optimum for picking up the image of the diffracted light, based on design information of the semiconductor wafer 2; and executing a control so as to rotate the illuminating unit 3 to the diffraction angle. An image signal output from the image pickup unit 4 is digitized by an A/D converter (not shown), and the image data is stored in the image memory 13.

The input unit 14 has a function of taking in various information such as design information of the semiconductor wafer 2 input from a predetermined database or input, for example, using a keyboard or mouse by an inspector, and a wavelength of the illuminating light output from the illuminating unit 3. It is to be noted that the design information includes a pattern pitch, reflectance, pattern shape, film thickness, and the like of the semiconductor wafer 2.

The diffraction angle calculation unit 16 obtains the angle of incidence of the illuminating light with respect to the semiconductor wafer 2, which is optimum for picking up the image of the diffracted light from the semiconductor wafer 2 by the image pickup unit 4, based on the design information of the semiconductor wafer 2 taken in from the input unit 14. Moreover, the diffraction angle calculation unit 16 obtains the diffraction angle of the desired ±n-dimensional diffracted light in the diffracted lights from the semiconductor wafer 2. In this case, the inspector operates the keyboard or mouse of the input unit 14 to set the desired ±n-dimensional diffracted light.

The diffraction angle calculation unit 16 has a function of calculating the angle of incidence of the illuminating light corresponding to the optimum diffraction angle with respect to the semiconductor wafer 2 whose image is picked up by the image pickup unit 4 as described above. Concretely, for example, the primary diffraction angle can be obtained by calculation of the following equation (1). That is, assuming that the diffraction angle is $\theta_d$, the angle of incidence of the illuminating light is $\theta_i$, a diffraction order is m, the pattern pitch of the semiconductor wafer 2 is p, and the wavelength of the illuminating light is $\lambda$, the following equation results:

$$\sin \theta_d - \sin \theta_i = m\lambda/p \tag{1}$$

The diffraction angle calculation unit 16 calculates the above equation (1) to obtain the diffraction angle $\theta_d$.

It is to be noted that the above equation (1) is derived as follows. For diffraction conditions, the diffracted light generated from a plane lattice (pattern) including a two-dimensional period structure satisfies the following condition.

$$K_d' = +K_i'G \tag{2}$$

$K_i'$: component parallel to a lattice plane of a wave number vector $K_i$ of the incident light (illuminating light)

$K_d'$: component parallel to the lattice plane of a wave number vector $K_d$ of the diffracted light G: inverted lattice vector of the plane lattice Here, when the plane lattice is limited to a one-dimensional lattice, and an incidence surface is a plane vertical to a length direction of the lattice, the equation (2) turns to the following:

$$n_d k_0 \sin \theta_d = n_i k_0 \sin \theta_i + mK \tag{3},$$

$n_i$: refractive index on the incidence side, $n_d$: refractive index on the diffraction side, $\theta_i$: angle of incidence, $\theta_d$: diffraction angle, wherein:

$k_0 = 2Q/\lambda_0$, $\lambda_0$: wavelength of the light (in vacuum);

$K = 2Q/p$, p: period of lattice (pattern pitch);

m: diffraction order;

$n_d = n_i = 1$, and the equation (3) turns to the following:

$$\sin \theta_d - \sin \theta_i = m\lambda/p.$$

Figure 2:
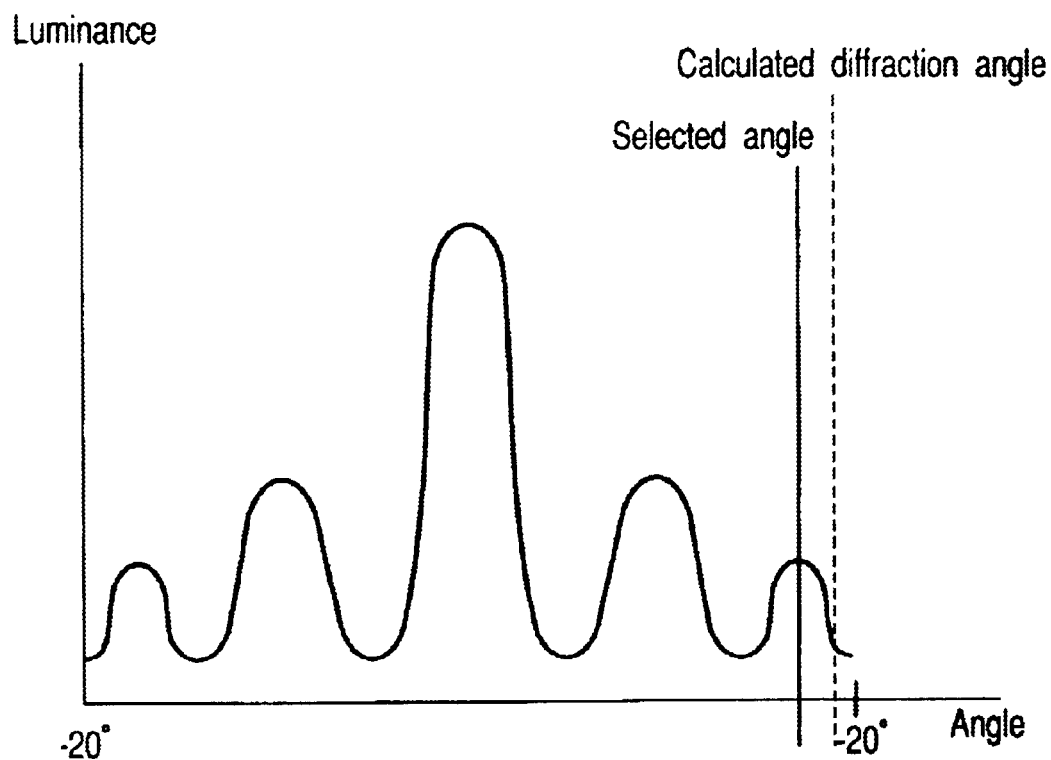
FIG. 2 is a luminance distribution diagram obtained when the angle of an illuminating light is varied in the defect detection apparatus according to the embodiment of the present invention.

When the angle of incidence of the illuminating unit 3 is varied, for example, in a range of +20° to −20°, the luminance distribution calculation unit 17 reads the image data obtained by the image pickup in the image pickup unit 4 from the image memory 13, and obtains an actual luminance distribution with respect to the angle of incidence of the illuminating light shown in FIG. 2 from the image data.

The illuminating setting unit 18 sends a command for setting the angle of incidence of the illuminating unit 3 corresponding to an m-dimensional diffraction angle calculated by the diffraction angle calculation unit 16 to the illuminating angle control unit 8 via the output unit 15. Moreover, the illuminating setting unit 18 compares the actual luminance distribution obtained by the luminance distribution calculation unit 17 with the diffraction angle calculated by the diffraction angle calculation unit 16, and selects an angle of a luminance peak in the luminance distribution which agrees with or is closest to this diffraction angle as the diffraction angle. The illuminating setting unit 18 sends a command for setting the angle of incidence of the illuminating unit 3 to the selected diffraction angle to the illuminating angle control unit 8 via the output unit 15.

In accordance with the instruction from the illuminating setting unit 18, the illuminating angle control unit 8 rotates the illuminating unit 3 so as to obtain the diffraction angle optimum for picking up the image of the diffracted light in the image pickup unit 4 and sets the angle of incidence with respect to the semiconductor wafer 2. Moreover, the illuminating angle control unit 8 and stage transfer rotation control unit 6 also have a function of integrally rotating the illuminating unit 3 in a parallel state with the semiconductor wafer 2 above the semiconductor wafer 2 and two-dimensionally varying a direction in which the semiconductor wafer 2 is irradiated with the illuminating light. It is to be noted that instead of varying the direction for irradiating the semiconductor wafer 2 with the illuminating light by the illuminating angle control unit 8, the stage transfer rotation control unit 6 rotates the stage 1, and the direction in which the semiconductor wafer 2 is irradiated with the illuminating light may also two-dimensionally be varied.

After setting the illuminating unit 3 to the angle of incidence with respect to the semiconductor wafer 2 so that the optimum diffracted light is taken into the image pickup unit 4, the defect inspection unit 19 reads the image data obtained by the image pickup in the image pickup unit 4 from the image memory 13, and image-processes the image data to detect the defects such as the damage, dust, surface irregularity, and dirt in the surface of the semiconductor wafer 2. The inspection result memory 20 stores information such as a type, number, position, and area of the defects detected by the defect inspection unit 19. The image display unit 5 displays the information such as the type, number, position, and area of the defects detected by the defect inspection unit 19.

The stage transfer rotation control unit 6 moves the stage 1 on which the semiconductor wafer 2 is laid in one direction (X direction) at a pitch synchronized with the image pickup in the image pickup unit 4, and also controls the rotating and positioning of the stage 1. To rotate the semiconductor wafer 2, the stage 1 itself can also be rotated, but it is preferable to dispose a rotary stage on which the semiconductor wafer 2 is to be laid on the stage 1 movable along one axis and to rotate the rotary stage.

The optical system control unit 7 controls the light amount of the illuminating unit 3, and executes a control to insert an interference filter (not shown) in acquiring an interference image. The illuminating angle control unit 8 controls the angle of incidence with respect to the semiconductor wafer 2 surface of the illuminating unit 3 in response to the instruction of the main control unit 11 as described above. The substrate conveyance unit 9 takes the semiconductor wafers 2 one by one from a storage stacker (cassette) (not shown) to lay the wafer on the stage 1, and returns the semiconductor wafer 2 on the stage 1 into the stacker after the defect inspection.

Operation of the defect detection apparatus configured as described above will be described hereinafter. First, the substrate conveyance unit 9 removes the semiconductor wafer 2 which is the inspection object from the stacker (not shown), and conveys and lays the wafer onto the stage 1. Subsequently, the stage transfer rotation control unit 6 positions the stage 1 on which the semiconductor wafer 2 is laid. Thereafter, the following defect inspection method is executed with respect to the semiconductor wafer 2.

A first defect inspection method will be described. First, the method comprises: taking the design information of the semiconductor wafer 2, such as the pattern pitch, reflectance, pattern shape, and film thickness of the semiconductor wafer 2, and the wavelength of the illuminating light output from the illuminating unit 3 into the detection apparatus main body 10 via the input unit 14 from a predetermined database or by the operation of the keyboard or mouse by the inspector. This design information of the semiconductor wafer 2 is sent to the diffraction angle calculation unit 16.

The main control unit 11 reads the program in the program memory 12, and instructs the diffraction angle calculation unit 16, illuminating setting unit 18, and defect inspection unit 19 to operate. The diffraction angle calculation unit 16 calculates the equation (1) based on the design information of the semiconductor wafer 2 taken in from the input unit 14, and obtains the angle of incidence and illuminating direction of the illuminating light with respect to the semiconductor wafer 2, which are optimum for picking up the image of the primary diffracted light from the semiconductor wafer 2 by the image pickup unit 4. For example, with respect to the semiconductor wafer 2 in which patterns such as DRAM are regularly arranged, the diffraction angle calculation unit 16 performs the calculation corresponding to a narrowest pattern pitch. Moreover, with respect to the semiconductor wafer 2 in which the patterns such as LSI are irregularly arranged, the diffraction angle calculation unit 16 performs the calculation corresponding to the pattern pitch at which a broad inspection is possible.

Next, the illuminating setting unit 18 receives the angle of incidence corresponding to the m-dimensional diffraction angle calculated by the diffraction angle calculation unit 16, and sends the command of the angle of incidence to the illuminating angle control unit 8 via the output unit 15. Thereby, the illuminating unit 3 is set to the instructed angle of incidence by the driving of the illuminating angle control unit 8. In this case, if there is an instruction of the two-dimensional direction to irradiate the semiconductor wafer 2 with the illuminating light, the illuminating angle control unit 8 integrally rotates the illuminating unit 3 in the parallel state with the semiconductor wafer 2 above the semiconductor wafer 2, or rotates the stage 1 and varies the direction to irradiate the semiconductor wafer 2 with the illuminating light.

In this state, the illuminating light is output from the illuminating unit 3 under the control of the optical system control unit 7 by the instruction of the main control unit 11. Then, the semiconductor wafer 2 is irradiated with the illuminating light with the optimum angle of incidence and illuminating direction to take in the m-dimensional diffracted light generated by the pattern of the chip formed in the semiconductor wafer 2 or the difference of the pitch. It is to be noted that fine adjustment is sometimes necessary for the angle of incidence of the illuminating unit 3 automatically set by an error between the manufactured semiconductor wafer 2 and design information as described above. In this case, the inspector sends the command of the fine adjustment to the illuminating angle control unit 8 from the input unit 14 via the output unit 15. Thereby, the angle of the illuminating unit 3 is adjusted in response to the instruction by the driving of the illuminating angle control unit 8.

The image of the diffracted light or interference light from the semiconductor wafer 2 is picked up by the image pickup unit 4, and the image signal is output from the image pickup unit 4. The image signal is digitized by the A/D converter (not shown), and stored as the image data in the image memory 13 of the detection apparatus main body 10.

The defect inspection unit 19 reads the image data obtained by the image pickup of the image pickup unit 4 from the image memory 13, image-processes the image data, and detects the defects such as the damage, dust, surface irregularity, and dirt in the surface of the semiconductor wafer 2. The defect inspection unit 19 stores the information of the detected defect in the inspection result memory 20, and displays the information in the image display unit 5.

Next, a second inspection method will be described. First, the method comprises: taking the design information of the semiconductor wafer 2, such as the pattern pitch, reflectance, pattern shape, and film thickness of the semiconductor wafer 2, and the wavelength of the illuminating light output from the illuminating unit 3 into the detection apparatus main body 10 via the input unit 14 from the predetermined database or by the operation of the keyboard or mouse by the inspector. This design information of the semiconductor wafer 2 is sent to the diffraction angle calculation unit 16.

The main control unit 11 reads the program in the program memory 12, and instructs the diffraction angle calculation unit 16, luminance distribution calculation unit 17, illuminating setting unit 18, and defect inspection unit 19 to operate. The diffraction angle calculation unit 16 calculates the above equation (1) to obtain the angle of incidence and incidence direction of the illuminating light with respect to the semiconductor wafer 2, which are optimum for picking up the image of the primary diffracted light from the semiconductor wafer 2 by the image pickup unit 4, based on the design information of the semiconductor wafer 2 taken in from the input unit 14.

Next, the main control unit 11 issues a command for varying the angle of incidence of the illuminating unit 3, for example, in a range of +20° to −20° to the illuminating angle control unit 8 via the output unit 15. Thereby, by the driving of the illuminating angle control unit 8, the angle of incidence of the illuminating light with which the surface of the semiconductor wafer 2 is irradiated from the illuminating unit 3 is varied in the range of +20° to −20°. At this time, the image pickup unit 4 picks up the image of the diffracted light from the semiconductor wafer 2, and outputs the image signal. The image signal is digitized by the A/D converter (not shown), and stored as the image data in the image memory 13 of the detection apparatus main body 10.

Next, the luminance distribution calculation unit 17 reads the image data at the time when the angle of the illuminating unit 3 is varied in the range of +20° to −20° as described above from the image memory 13, and obtains the actual luminance distribution with respect to the angle of incidence of the illuminating light from the image data as shown in FIG. 2.

Next, the illuminating setting unit 18 compares the actual luminance distribution obtained by the luminance distribution calculation unit 17 with the angle of incidence calculated by the diffraction angle calculation unit 16, and selects the angle of the luminance peak in the luminance distribution which agrees with or is closest to this angle of incidence as the diffraction angle. The illuminating setting unit 18 sends the command for setting the angle of incidence of the illuminating unit 3 corresponding to the selected diffraction angle to the illuminating angle control unit 8 via the output unit 15. Thereby, the angle of incidence of the illuminating unit 3 is set to the diffraction angle instructed by the driving of the illuminating angle control unit 8. In this case, if there is the instruction of the two-dimensional direction to irradiate the semiconductor wafer 2 with the illuminating light, the illuminating angle control unit 8 integrally rotates the illuminating unit 3 in the parallel state with the semiconductor wafer 2 above the semiconductor wafer 2, or rotates the stage 1 and varies the direction to irradiate the semiconductor wafer 2 with the illuminating light.

In this state, the illuminating light is output from the illuminating unit 3 under the control of the optical system control unit 7 by the instruction of the main control unit 11. Then, the semiconductor wafer 2 is irradiated with the illuminating light with the optimum angle of incidence and illuminating direction to take in the diffracted light generated by the pattern of the chip formed in the semiconductor wafer 2 or the difference of the pitch. It is to be noted that the fine adjustment is sometimes necessary for the angle of incidence of the illuminating unit 3 automatically set by the error between the manufactured semiconductor wafer 2 and design information as described above. In this case, the inspector sends the command of the fine adjustment to the illuminating angle control unit 8 from the input unit 14 via the output unit 15. Thereby, the angle of the illuminating unit 3 is adjusted in response to the instruction by the driving of the illuminating angle control unit 8.

The image of the diffracted light or interference light from the semiconductor wafer 2 is picked up by the image pickup unit 4, and the image signal is output from the image pickup unit 4. The image signal is digitized by the A/D converter (not shown), and stored as the image data in the image memory 13 of the detection apparatus main body 10.

The defect inspection unit 19 reads the image data obtained by the image pickup of the image pickup unit 4 from the image memory 13, image-processes the image data, and detects the defects such as the damage, dust, surface irregularity, and dirt in the surface of the semiconductor wafer 2. The defect inspection unit 19 stores the information of the detected defect in the inspection result memory 20, and displays the information in the image display unit 5.

In the first and second inspection methods, the diffraction angle calculation unit 16 obtains the optimum angle of incidence and illuminating direction of the illuminating unit 3 for picking up the image of the diffracted light based on the design information of the semiconductor wafer 2. However, when diffracted lights other than the diffracted light obtained by setting the automatically set diffraction angle are easily observed depending on the type of the semiconductor wafer 2, the inspector operates the keyboard or mouse in the input unit 14 to designate the desired n-dimensional diffracted light to the effect. Thereby, the diffraction angle calculation unit 16 obtains the optimum angle of incidence and illuminating direction of the illuminating unit 3 for picking up the image of the designated n-dimensional diffracted light based on the design information of the semiconductor wafer 2.

Moreover, in the chip pattern formed in the semiconductor wafer 2, which has two directions, the diffraction angle calculation unit 16 can obtain the angle of incidence and illuminating direction of the illuminating unit 3 with which the diffracted lights of the respective chips can both be observed by the image pickup unit 4 in both directions based on the design information of the semiconductor wafer 2.

In this case, the image of the diffracted light generated by the illuminating light output from the illuminating unit 3 which has been set is picked up by the image pickup unit 4. The image data is image-processed by the defect inspection unit 19, and the defects of each chip such as the damage, dust, surface irregularity, and dirt can be detected in the semiconductor wafer 2 surface of the chip pattern which has two directions.

Moreover, in the semiconductor wafer 2 including a three-dimensional hierarchy structure, the diffraction angle calculation unit 16 can calculate the diffraction angle in each layer based on the film thickness of the design information. Thereby, without calculating the angle of the diffracted light by an influence of a substrate of the semiconductor wafer 2, the diffraction angle is calculated with respect to the diffracted light generated by the influence of the surface layer, and the image can be picked up.

Furthermore, the stage transfer rotation control unit 6 can execute rotation control together with transfer control of the stage 1 as described above. For the rotation control of the stage 1, the control is executed in accordance with the direction of the pattern of the semiconductor wafer 2 which is the inspection object. While the semiconductor wafer 2 surface is irradiated with the linear illuminating light from the illuminating unit 3, and the stage 1 is moved in a linear direction (X direction). In this case, it is sometimes impossible to pick up the image of the diffracted light depending on the direction of the pattern of the semiconductor wafer 2. For example, when the direction of the pattern crosses at 90° with respect to a line direction of the illuminating light, the image of the diffracted light cannot be picked up. In this case, the stage transfer rotation control unit 6 controls the rotation of the stage 1, and rotates the stage 1, for example, by 90° with respect to a vertical line of the center. Thereby, since the direction of the pattern of the semiconductor wafer 2 is the same as the line direction of the illuminating light, the image of the diffracted light can be picked up.

Additionally, the illuminating angle control unit 8 can three-dimensionally control the inclination angle of the illuminating unit 3 with respect to the semiconductor wafer 2 surface. In the above-described embodiment, since the inclination angle of the illuminating unit 3 with respect to the semiconductor wafer 2 surface is two-dimensionally controlled, the image of the diffracted light cannot necessarily be picked up in a high directivity state. However, since the illuminating unit 3 is three-dimensionally operated, the image of the diffracted light having a highest directivity can be picked up in accordance with the pattern of the semiconductor wafer 2. Thereby, the image of the diffracted light can be picked up from the pattern which has not been captured only by two-dimensionally controlling the inclination angle. Moreover, even when the stage transfer rotation control unit 6 controls and three-dimensionally rocks the stage 1 instead of three-dimensionally controlling the illuminating unit 3, the similar effect can be obtained.

Moreover, the illuminating unit 3 can be applied to not only the irradiation with the linear illuminating light but also the irradiation with a radial illuminating light. In this case, the radial illuminating light is converted to the line shape in the lens.

It is to be noted that in the above-described present embodiment the semiconductor wafer 2 has been described as the inspection object, but the present defect detection apparatus can also be applied, for example, to the defect inspection of the damage, dust, surface irregularity, and dirt in a glass substrate surface of a flat display such as a liquid crystal display.

As described above, in the present embodiment, the method comprises: obtaining the angle of incidence of the illuminating light with respect to the semiconductor wafer 2, which is optimum for picking up the image of the diffracted light, based on the design information of the semiconductor wafer 2 (e.g., the pattern pitch, reflectance, pattern shape, and film thickness of the semiconductor wafer 2, or the wavelength of the illuminating light output from the illuminating unit 3); and setting the angle of incidence or illuminating direction of the illuminating unit 3 to the calculated angle of incidence. Thereby, for example, even when the angle and direction to take in the primary diffracted light change because of the pattern of the chip formed in the semiconductor wafer 2 or the difference of the pattern design of the pitch, the illuminating unit 3 can automatically be set to the optimum angle of incidence and illuminating direction for taking in the primary diffracted light, and much time is not required in the inspection.

Moreover, when the other n-dimensional diffracted lights are more easily observed depending on the type of the semiconductor wafer 2, the desired n-dimensional diffraction data is designated by the input unit 14, and thereby the angle of incidence of the illuminating unit 3 and direction optimum for picking up the image of the diffracted light can be obtained based on the design information of the semiconductor wafer 2.

Furthermore, with respect to the chip pattern formed in the semiconductor wafer 2, which has two directions, the angle of incidence and direction of the illuminating unit 3 can be obtained based on the design information of the semiconductor wafer 2 so that the diffracted lights of the respective chips of the opposite directions can both be observed.

Additionally, the actual luminance distribution obtained by the luminance distribution calculation unit 17 is compared with the diffraction angle calculated by the diffraction angle calculation unit 16, the angle of the luminance peak in the luminance distribution which agrees with or is closest to this diffraction angle is selected as the diffraction angle, and the angle of incidence of the illuminating unit 3 is set so as to correspond to the diffraction angle. Thereby, for example, even when the diffraction angle and diffraction direction to take in the primary diffracted light change because of the pattern of the chip formed in the semiconductor wafer 2 or the difference of the pitch, the illuminating unit 3 can automatically be set to the angle of incidence and illuminating direction optimum for taking in the primary diffracted light from a self-measured luminance distribution, and much time is not required in the inspection.

The present invention is not limited only to the above-described embodiment, and can appropriately be modified and carried out in a range in which the scope is not changed.

According to the present invention, there can be provided a defect detection apparatus in which an illuminating light can be set to an optimum angle for taking in a diffracted light necessary for performing inspection.

Moreover, according to the present invention, there can be provided a storage medium readable by a computer, in which program for setting the illuminating light to the optimum angle for taking in the diffracted light necessary for performing the inspection is stored.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A defect detection apparatus comprising: an illuminating unit which irradiates an inspection object with illuminating light; and an image pickup unit which picks up an image of a diffracted light from the inspection object to perform defect inspection of the inspection object from image data picked up by the image pickup unit, the apparatus further comprising:

a diffraction angle calculation unit to obtain an angle of incidence of the illuminating light with respect to the inspection object, which is optimum for picking up the image of the diffracted light, based on design information of the inspection object;

an illuminating angle control unit which changes an angle of incidence of the illuminating unit with respect to the inspection object;

a luminance distribution calculation unit which obtains a luminance distribution with respect to the angle of incidence from the image data of the image pickup unit obtained by varying the angle of incidence of the illuminating unit with respect to the inspection object by the illuminating angle control unit; and an illuminating setting unit to compare the luminance distribution obtained by the luminance distribution calculation unit with the angle of incidence calculated by the diffraction angle calculation unit and to set the illuminating unit to the angle of incidence corresponding to a luminance peak in the luminance distribution which is closest to the calculated angle of incidence.

2. A defect detection apparatus according to claim 1, wherein the diffraction angle calculation unit obtains the angle of incidence of the illuminating light with respect to the inspection object based on design information of the inspection object and a diffraction order of designated diffracted light.

3. A defect detection apparatus according to claim 1, wherein the diffraction angle calculation unit calculates the diffraction angle with respect to a surface layer based on a film thickness of the design information with respect to a hierarchy structure of the inspection object.

4. A defect detection apparatus according to claim 1, wherein the illuminating angle control unit comprises an input unit which finely adjusts the angle of incidence of the illuminating unit set by the illuminating setting unit.

5. A defect detection apparatus according to claim 1, wherein the design information of the inspection object comprises at least one of pattern pitch, reflectance, pattern shape, film thickness, and wavelength of the illuminating light.

6. A defect detection apparatus according to claim 1, wherein the diffraction angle calculation unit assumes that the diffraction angle is $\theta_d$, the angle of incidence of the illuminating light is $\theta_i$, a diffraction order is m, the pattern pitch of the inspection object is p, and a wavelength of the illuminating light is $\lambda$, calculates $$\sin \theta_d - \sin \theta_i = m\lambda/p,$$

and obtains the diffraction angle.

7. A defect detection apparatus according to claim 1, wherein the illuminating angle control unit further has a function of rotating and/or controlling the illuminating unit using a center of the inspection object as an axis, and two-dimensionally varies the angle of incidence and incidence direction of the illuminating unit with respect to the inspection object.

8. A defect detection apparatus according to claim 1, wherein the illuminating angle control unit further has a function of rotating and/or controlling a stage on which the inspection object is laid, and two-dimensionally varies the angle of incidence and incidence direction of the illuminating unit with respect to the inspection object.

9. A defect detection apparatus according to claim 1, wherein the illuminating unit comprises a line illuminating unit which irradiates the inspection object with linear illuminating, further the image pickup unit comprises a line sensor camera to pick up the image of the diffracted light by a line illuminating light with which the inspection object is irradiated, and further the inspection object is laid on a stage which is one-dimensionally driven in a direction intersecting the linear illuminating of the line illuminating unit.

10. A defect detection apparatus according to claim 9, wherein the one-dimensionally driven stage comprises a rotary stage on which the inspection object is laid, has a function of rotating and/or controlling the rotary stage, and rotates the inspection object with respect to an incidence direction of the illuminating unit.

11. A storage medium readable by a computer, in which a program is stored to irradiate an inspection object with illuminating light from an illuminating unit and to pick up an image of a diffracted light from the inspection object by an image pickup unit and to inspect the inspection object based on image data, the program allowing a computer to execute:

a step of calculating an angle of incidence of the illuminating light with respect to the inspection object, which is optimum for picking up the image of the diffracted light, based on design information of the inspection object;

a step of obtaining a luminance distribution with respect to the angle of incidence of the illuminating unit from the image data acquired by varying the angle of incidence of the illuminating unit with respect to the inspection object by the image pickup unit; and a step of obtaining an angle of a luminance peak which is closest to the calculated angle of incidence as the angle of incidence of the illuminating unit from the obtained luminance distribution to control the incidence angle of the illuminating unit.

* * * * *